(12) United States Patent
Spain et al.

(10) Patent No.: US 8,029,917 B2
(45) Date of Patent: Oct. 4, 2011

(54) COATED ARTICLES

(75) Inventors: Elliott Ashley Fielding Spain, Cambridge (GB); Junia Cristina Avelar Batista Wilson, Kettering (GB); Jonathan Housden, Royston (GB)

(73) Assignee: Tecvac Ltd., Cambridge (GB)

(*) Notice: Subject to any disclaimer, the term of this patent is extended or adjusted under 35 U.S.C. 154(b) by 893 days.

(21) Appl. No.: 12/068,844

(22) Filed: Feb. 12, 2008

(65) Prior Publication Data

US 2009/0198343 A1 Aug. 6, 2009

(30) Foreign Application Priority Data

Jan. 31, 2008 (GB) .................................. 0801725.3

(51) Int. Cl.
*B32B 15/01* (2006.01)

(52) U.S. Cl. ..... 428/673; 428/212; 428/704; 623/16.11; 623/18.11; 420/501

(58) Field of Classification Search .................. 428/615, 428/617, 655, 660, 662, 663, 666, 671, 673, 428/212, 704; 623/16.11, 18.11; 240/501; 420/501

See application file for complete search history.

(56) References Cited

U.S. PATENT DOCUMENTS

| | | | | |
|---|---|---|---|---|
| 4,403,014 | A | 9/1983 | Bergmann | 428/546 |
| 4,476,590 | A | 10/1984 | Scales et al. | 3/1.91 |
| 5,308,412 | A | 5/1994 | Shetty et al. | 148/238 |
| 5,649,951 | A | 7/1997 | Davidson | 606/198 |
| 5,800,559 | A | 9/1998 | Higham et al. | 623/23 |
| 5,945,153 | A | 8/1999 | Dearnaley | 427/2.12 |
| 5,984,905 | A | 11/1999 | Dearnaley | 604/265 |
| 6,361,567 | B1 | 3/2002 | Dearnaley | 623/23.73 |
| 2004/0119743 | A1 | 6/2004 | Xu | 345/760 |
| 2004/0131894 | A1 | 7/2004 | Erdemir et al. | 428/698 |
| 2005/0003239 | A1 | 1/2005 | Derflinger et al. | 428/698 |
| 2007/0065679 | A1 | 3/2007 | Strangman | 428/698 |

FOREIGN PATENT DOCUMENTS

| WO | WO 03/003950 A1 | 1/2003 |
|---|---|---|
| WO | WO 2007/147832 A1 | 12/2007 |

OTHER PUBLICATIONS

S.M. Aouadi et al.: Zirconium Nitride/Silver Nanocomposite Structures for Biomedical Application, Jun. 2004, J. Vac. Sci. Technol. B, vol. 3, No. 3, pp. 1134-1140.*

Mulligan et al., "CrN-Ag self-lubricating hard coatings", Surface & Coatings Technology, 200:1495-1500 (2005).

Bosetti et al., "Silver coated materials for external fixation devices: in vitro biocompatibility and genotoxicity", Biomaterials, 23;887-892 (2002).

(Continued)

*Primary Examiner* — Michael C Miggins

(74) *Attorney, Agent, or Firm* — Morgan, Lewis & Bockius LLP

(57) ABSTRACT

A metallic biomedical article, preferably an orthopaedic implant, instrument or tool, for use in contact with internal human body tissue, having a first silver containing metal nitride coating thereon, and process for making the same, is provided.

12 Claims, 2 Drawing Sheets

OTHER PUBLICATIONS de los Arcos et al., "Preparation and characterization of TiN-Ag nanocomposite films", Vacuum, 67:463-470 (2002).

Endrino et al., "Microstructure and vacuum tribology of TiC-Ag composite coatings deposited by magnetron sputtering-pulsed laser deposition", Surface and Coatings Technology, 157:95-101 (2002).

Yao et al., "Effect of Ag/W addition on the wear performance of CrN coatings prepared by RF unbalanced magnetron sputtering", Materials Science and Engineering, A 398:88-92 (2005).

Tse et al., "Nanometer-scale multilayer coatings combining a soft metallic phase and a hard nitride phase; study of the interface structure and morphology", Surface and Coatings Technology, 180-181:470-477 (2004).

Xiao et al., "Wetting of titanium nitride and titanium carbide by liquid metals", Acta mater, 44(1):307-314 (1996).

Yoshinari et al., "Influence of surface modifications to titanium on antibacterial activity in vitro", Biomaterials, 22;2043-2048 (2001).

* cited by examiner

COATED ARTICLES

TECHNICAL FIELD

The invention relates to metallic biomedical articles for use in contact with internal human or animal body tissue, particularly prosthetic implants, instruments and tools.

BACKGROUND

Metal articles are often used in contact with internal human or animal body tissue for a wide range of uses. However care must be taken, particularly if such articles are implanted into the human or animal body, that they are long-lasting, non-corrosive and do not leach metal ions into the body.

Orthopaedic implants (such as a replacement hip) conventionally employ a metal-on-polymer arrangement, but suffer from the disadvantage of wear-induced osteolysis associated with polyethylene debris, even with improved modern polyethylenes. Metal-on-metal prostheses offer an alternative without these disadvantages, potentially providing greatly increased dislocation resistance and a longer service life, opening up the technique for the young active category. However, because of the stresses encountered in orthopaedic implants, particularly in articulating orthopaedic implants, it would be beneficial to use coatings to reduce wear.

Additionally, the use of metal-on-metal orthopaedic implants can result in undesirable wear debris, at levels such that they are detectable in blood. For example, cobalt/chromium has been shown to provide a ten-fold increase in these potentially carcinogenic metal ions in the blood of a patient, compared to normal healthy subjects.

A coating for an articulating orthopaedic implant, must satisfy a number of additional demanding requirements, e.g. it must be hard, have low surface friction and also be tough enough to withstand potentially high impact forces over a long period of time. Coatings which are not tough enough (i.e. too brittle) or hard wearing enough may have a short service life or may even become detached, which could be catastrophic. It would be additionally advantageous if such coatings had anti-microbial properties.

It is becoming generally accepted that silver in ionic form has antimicrobial properties. Also very fine particles of silver e.g. nano-particles, have a surface area to volume ratio such that they can readily oxidise to form the ionic compound silver oxide which provides an antimicrobial effect. However, larger silver structures tend to be ineffective antimicrobials. It is therefore not simply a matter of using silver as a coating in order to provide an antimicrobial effect. In any case, silver is too soft for use as a coating in applications where a significant amount of stress is encountered, e.g. in articulating orthopaedic implants.

U.S. Pat. No. 6,361,567 discloses a process of forming an anti-microbial coating on a surface of a medical implant, which involves incorporating silver into a diamond-like carbon coating. However, whilst diamond-like carbon is very hard and has a low friction, it is often a brittle material. It is therefore not ideal for use as a coating especially in articulated prosthetic implants.

SUMMARY OF INVENTION

The present invention relates to a metallic biomedical article for use in contact with internal human or animal body tissue, having a first silver-containing metal nitride coating thereon.

It has been found, that such silver metal nitride coatings are hard, have low friction coefficient and are tough enough (i.e. not too brittle) to be used in a wide range of biomedical applications and also provide an anti-microbial effect.

The coated articles of the present invention are particularly suitable for use as implants, instruments and tools for the internal human or animal body, especially orthopaedic implants (e.g. prosthetic hips, knees, shoulders, ankles, spinal prostheses or parts thereof and the instruments and tools utilised e.g. during implant surgery).

The coated articles are especially suitable for use as articulating orthopaedic implants (e.g. prosthetic hips or parts thereof). As the coatings of the present invention are wear resistant, minimise metal ion leaching and are self-lubricating, they overcome the drawbacks of metal-on-metal articulating prosthetic implants. They therefore enable a significant improvement in joint replacement operations, extending service life and reducing post-operative complications.

The silver metal nitride coatings of the articles of the present invention are believed to derive some of their attractive properties from the fact that silver has been found to be insoluble in metal nitride materials. It is believed that the silver forms nanoparticles and that the structure of the coating is columnar in nature. It is believed that the anti-microbial properties of the articles according to the invention arise because silver exists in small, often nano-particle form on the surface of the coated article. Furthermore it is believed that as the silver particles are worn or dissolved away from the surface, the antimicrobial capability is renewed by silver particles migrating to the surface of the coated article.

The metallic articles may be made from a wide range of materials, for example titanium and its alloys, zirconium and its alloys, cobalt/chromium based alloys or stainless steel.

Preferred metal nitride coatings are of the form $(A_x B_y C_z)Q$-Ag, where Q is selected from N, CN, BN, CBN, NO, CNO, BNO, CBNO and A, B and C are independently selected from Ti, Al, Cr, Zr, Ta, Y, W, Pt, Au, Cu, Si, Nb and B and where $0.25 < x+y+z < 4.0$. Preferably Q is selected from N, CN, BN, NO and A, B and C are independently selected from Ti, Cr, Zr, Si and Al. More preferably Q is selected from N, CN, NO and A, B and C are independently selected from Ti, Cr, Zr. Currently most preferred is $Cr_xN$—Ag and $Cr_xNO$—Ag.

It has been found that the presence of silver in the coating reduces its hardness, and can provide a self-lubricating surface. Therefore, the quantity of silver can be selected in order to tailor the mechanical properties of the coating and levels in the range of from 0.1 to 99 at %, from 0.5 to 35 at %, or even from 1.0 to 25 at % have been found to provide a good balance of properties.

The coatings of the present invention may be formed onto the metallic articles by a wide range of techniques known to the person skilled in the art. Deposition of the coating using a physical vapour deposition (PVD) and/or a chemical vapour deposition (CVD) method particularly favoured. Electron beam plasma-assisted PVD is currently the most preferred process. Suitable PVD processes include electron-beam evaporation, magnetron sputtering and arc evaporation.

Thus, in another aspect, the present invention relates to a method of coating a metallic biomedical article for use in contact with internal human or animal body tissue, by depositing a silver-containing metal nitride on its surface.

The metallic articles of the present invention may desirably have more than one coating on their surface. In particular, it has been found to be particularly advantageous to have two silver containing metal nitride coatings having different quantities of silver, particularly where the outermost coating contains a higher quantity of silver than the coating underneath. Such an arrangement provides a strong anti-microbial effect at the surface and provides good self-lubrication and self-conforming properties, which are particularly advantageous during the initial phase following the implant of an articulating orthopaedic implant.

It is also possible for the coating to be a gradient coating with the silver or other elemental content that is incremented or decreased toward the surface, bringing about a progressive change in the layer composition, for instance by a continuous or stepwise adjustment. For example, a coating where the silver content increases towards the coating surface may be particularly advantageous.

The thickness of the coating or coatings can very widely according to the application, but is typically within the range of from 0.1 to 100 micrometers, preferably from 0.5 to 50 micrometers, more preferably from 1.0 to 20 micrometers.

Other layers and coatings may be present, for example an inner layer to improve corrosion resistance and hence reduce metal ion leaching, which may be pure metal nitride, e.g. chromium nitride, or pure metal, e.g. chromium.

The invention will now be illustrated by way of example, with reference to the accompanying drawings, in which.

EXPERIMENTAL PROCEDURE

Figure 1:
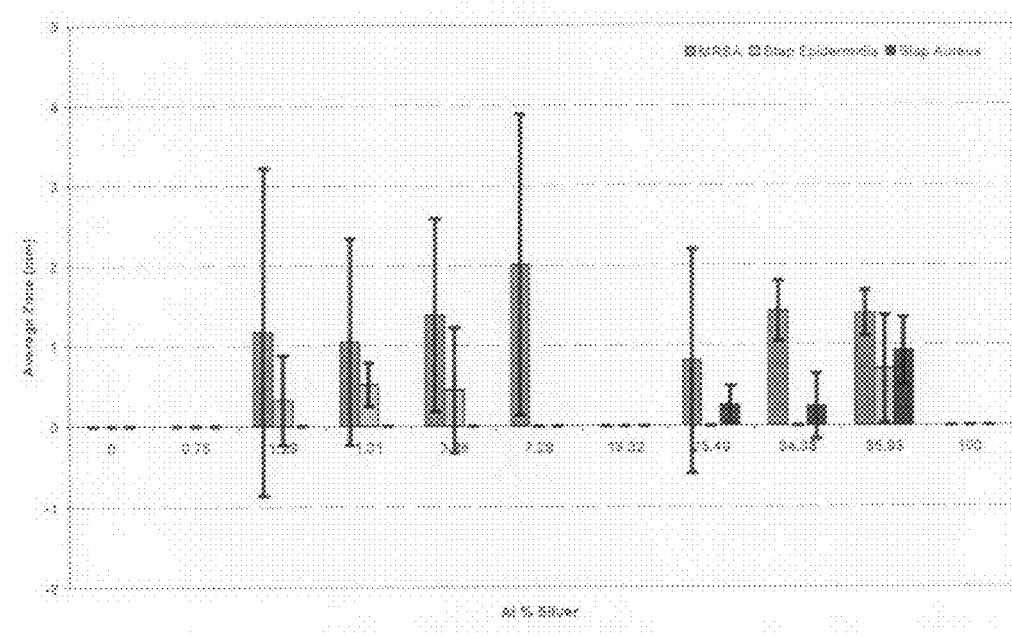
FIG. 1 is a chart showing the average areas of the zones of inhibition produced by CrN—Ag coating in direct contact with three different micro-organisms: *Staphylococcus aureus* (MRSA), *Staphylococcus aureus*, and *Staphylococcus epidermis*.

Experiments are carried out according to the following procedure.

20 and 30 mm diameter mirror polished and hardened AISI M2 steel test discs are used as the articles to be coated. The articles are first ultrasonically cleaned in alkaline solution and then placed in a Tecvac IP90 twin electron beam deposition chamber. The coating deposition cycle consists of five sequential steps:
1) Pump and heating with radiant heaters
2) Sputter cleaning in any diode inert (preferably argon) glow discharge
3) Plasma heating in any inert (preferably argon) glow discharge assisted by thermionic source to heat the workpiece (articles) up to the processing temperature
4) Silver metal-nitride deposition
5) Cooling in any inert gas, nitrogen or mixture of inert gas and nitrogen without any glow discharge assistance.

Pump and Heating

With the radiant heaters switched on the chamber is pumped down to pressures lower than $5 \times 10^{-3}$ Pa with the temperature of the articles is to be greater than 280° C.

Sputter Cleaning

Articles to be treated are subjected to a sputter clean step using any inert gas (preferably argon) discharge in diode configuration for 5-15 minutes (preferably 5 minutes). A D.C. power supply is used to negatively bias the article, although R.F. or microwave power supplies may be used.

The chamber is back filled to an argon pressure of 1.0-5.0 Pa (typically 2.0 Pa) and the bias voltage ranges from −600 V to −2000 V (typically −1000 V).

Plasma Heating

Inert gas (typically argon) pressure is set between 0.1-1.0 Pa (preferably 0.3 Pa). Workpiece bias during plasma heating is to be set to between −600 V to −2000 V (typically −1000 V). A negatively biased tungsten filament is utilised as a third electrode to emit electrons into the glow discharge. A high current, low voltage power supply is used to heat the filament so that electrons are thermionically emitted into the glow discharge. The filament is also negatively biased using a D.C. high current, low voltage power supply so that the electrons leave the filament with appreciable energy to enhance ionisation levels in the discharge. The filament heater current may vary from 40 A to 150 A depending on level of ionisation required. The filament bias may vary between −50 V to −200 V (typically −100 V). Radiant heaters are optionally utilised to help achieve the treatment temperature, usually between 280° C. and 500° C. typically 350° C.

Silver Metal-Nitride Deposition

Inert gas (typically argon) pressure is set to between 0.1-1.0 Pa (typically 0.3 Pa). Workpiece bias during deposition is reduced to between −25 to −100 V. The negatively biased filament is continued to be utilised during the deposition process. Its heater current may vary from 40 A to 150 A depending on the level of ionisation required. The filament bias remains the same as that selected for the plasma heating stage.

Silver metal nitrides are grown using silver, another metal or combination of metals and other non metallic elements, for example titanium, chromium, zirconium, silicon, aluminium and combinations thereof and reactive gas, nitrogen or any combination of nitrogen plus reactive gases (e.g. CN, BN, CBN, NO, CNO, BNO or CBNO). The preferred metal is chromium although any combination of metals and non metallic elements can be used.

Silver metal-nitride thin films are grown using electron beam plasma assisted physical vapour deposition. The film is made up of a number of layers. Firstly a metallic, e.g. titanium, chromium or zirconium (typically chromium) bond layer is deposited onto the article by means of electron beam evaporation. To further enhance the adhesion of the bond layer, the crucibles in which the source materials are held are positively biased between +25 to +100 V. The rate of deposition of the bond layer is controlled by optical emission spectroscopy. A chosen wavelength is monitored and a defined count level is maintained. The deposition time for this bond layer may vary from 3 to 15 minutes, typically 5 minutes.

The next layer is the first metal-nitride layer; reactive gas nitrogen or combination of nitrogen plus other reactive gases is admitted into the chamber at a flow rate from 10 to 200 ml/min (typically 60 ml/min). As the addition of reactive gas(es) will increase the chamber pressure, the new pressure is controlled by the level of metal evaporated by the electron beam gun and is maintained at a chosen value. The deposition time for this layer can vary from 5 to 100 minutes.

The next layer involves the grading-in of silver to a chosen metal to silver ratio. The amount of silver deposited is controlled by electron beam evaporation; to get to the chosen metal-to-silver ratio, the current of the electron beam is gradually altered. The metal-to-silver ratio is monitored by optical emission spectroscopy. Each metal has a different selected wavelength, so the ratio is calculated by dividing the number of counts at each particular metals selected wavelength by the umber of counts at silver's selected wavelength. The deposition time for this grading can vary from 1 to 10 minutes, typically 5 minutes. Whilst grading the silver to the chosen ratio, the chamber pressure is maintained at the chosen value by altering the levels of metal evaporation. The next layer is the final top layer and is a silver metal-nitride layer. It is deposited using the chamber pressure and metal-to-silver ratio chosen in the grading layer stage. The deposition time for this layer can vary from 5 to 1200 minutes, preferably 120 minutes.

The ratio of metal to silver can be altered throughout the deposition of the final layer. This is achieved by repeating the grading layer process. The ratio can be changed an indefinite number of times throughout the deposition of the layer.

Cooling

After coating deposition, a backfill gas (any inert gas, nitrogen or mixture of inert gas and nitrogen) is admitted into the chamber up to a pressure $10^2$ Pa. When the article temperature is below 200° C., backfill gas is further admitted into the chamber until atmospheric pressure is reached.

Example 1

CrN—Ag Deposition: Effect of Metal to Silver Ratio

CrN—Ag was deposited on AISI M2 steel test discs at 9 different relative OES peak height chromium to silver ratios (2.0, 1.75, 1.5, 1.25, 1.0, 0.75, 0.5, 0.25, 0.1). Pure CrN and pure silver coating were also deposited for comparison. Mirror polished and hardened AISI M2 steel test discs were ultrasonically cleaned in an alkaline solution and placed within the Tecvac IP90 deposition chamber. After an ultimate pressure lower than $5.0 \times 10^{-3}$ Pa and a workpiece temperature greater than 330° C. were reached, the chamber was backfilled with argon to a pressure of 2.0 Pa to carry out the sputter cleaning step. The test discs were biased at −1000 V and sputter cleaned for 5 minutes. Plasma heating was performed for 5 minutes at a chamber pressure of 0.3 Pa with the workpiece bias remaining the same. The tungsten filament was biased at −100 V and the filament heater current was increased to 55 A.

The next stage was deposition of the silver metal-nitride film. This is broken down into a number of steps: Firstly the workpiece biased was dropped to −50 V, the filament heater current was increased to 71 A and the crucible bias was set to 50 V. The chromium slug was heated with the electron beam until it started to sublime. The optical emission spectrometer registered the chromium within the plasma and a numerical value for the number of chromium counts is displayed with its software. The electron beam current was increased to increase the rate of sublimation and therefore raise the amount of chromium within the plasma; the level of chromium was set at a fixed OES count of approximately 8000 and held for 5 minutes to ensure the deposition of a suitably thick metallic bond layer. After 5 minutes of chromium deposition the chamber was backfilled with nitrogen at a flow rate of 60 m/min. The chamber pressure increased as the nitrogen was introduced. After 10 minutes of CrN deposition, the silver slug was heated by a second electron beam and slowly graded in over 5 minutes to the required chromium (metal) to silver ratio. The ratio and total pressure were maintained for the remainder of the coating cycle. Finally, treated discs were cooled as described above. This process was repeated for all the chosen ratios, resulting in 11 sets of test discs (including pure CrN and pure silver).

The effect of silver concentrations on the antimicrobial behaviour of the silver metal-nitride coating is shown in FIG. 1. This figure displays the results of zone of inhibition: direct contact testing using 3 different micro-organisms, *Staphylococcus aureus* (MRSA), *Staphylococcus aureus* and *Staphylococcus epidermis*. The values on the chart are the average zones of inhibition measured once the test pieces had been evaluated, it can be clearly seen that both pure CrN and pure silver have no antimicrobial effects. The effect of adding silver to the metal-nitride results in some antimicrobial behaviour for most of the concentrations on at least one of the micro-organisms.

Figure 2:
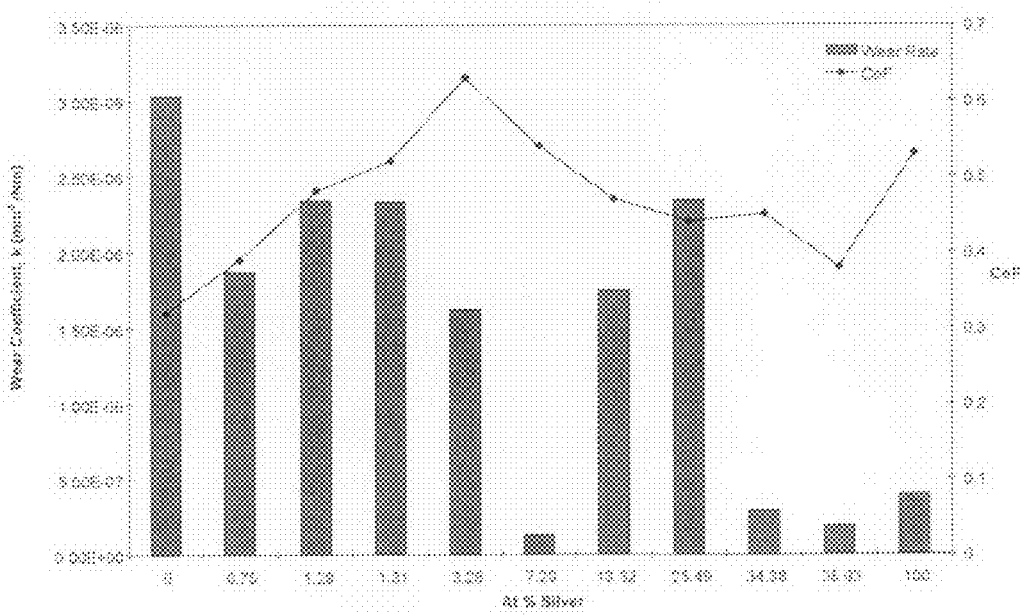
FIG. 2 is a chart which shows the wear rate, k, and the coefficient of friction for CrN—Ag coatings.

The effect of silver concentrations on the wear and friction behaviour of silver metal-nitrides is shown in FIG. 2. The figure shows that as the atomic percent of silver increases the wear coefficient; k reduces by at least 1 order of magnitude to a minimum at 7.29 at. % silver. As the atomic percentage of silver increases further the wear coefficient increases and then drops at level over 34.38 at. % silver. Pure silver shows a wear rate lower than that of pure CrN but is slightly higher than that of CrN—Ag with 7.29, 34.38 and 35.93 at. % silver. These results show that adding silver to metal-nitrides reduces the wear coefficient by up to 1 order of magnitude which would suggest that as the coating wears the silver acts as a solid lubricant resulting in a self-lubricating surface. The coefficient of friction also increases as the levels of silver increase to a maximum at 3.28 at. % silver, as the level of silver increases further the friction coefficient drops.

Figure 3:
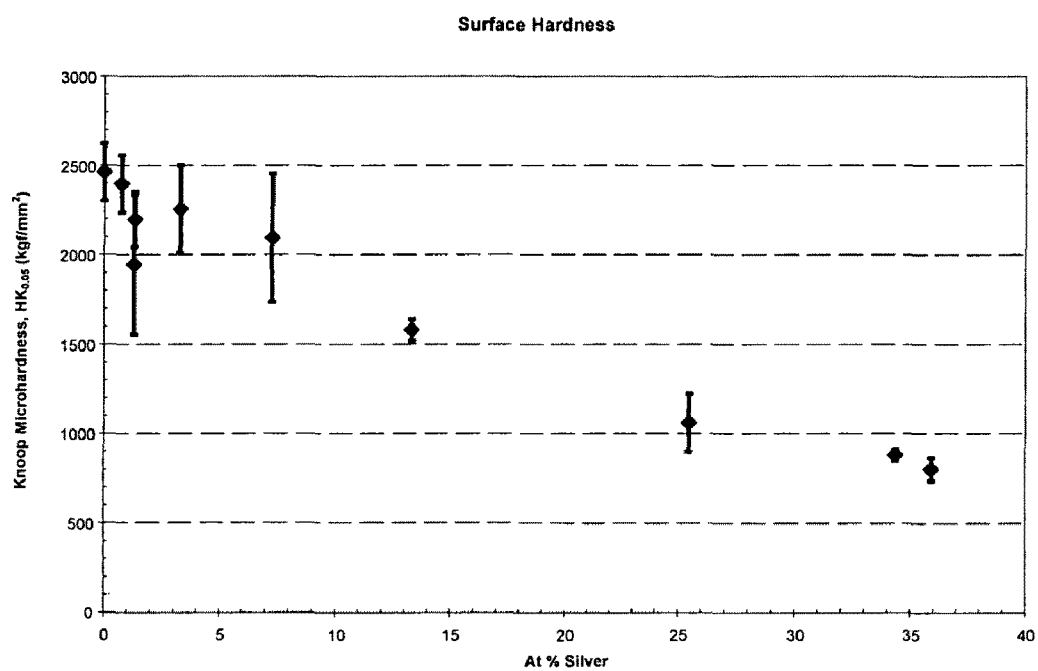
FIG. 3 is a chart showing the Knoop surface micro-hardness at a 50 μm load for CrN—Ag coatings.

Adding silver to chromium-nitride results in the reduction of surface hardness, this is illustrated in FIG. 3. This figure shows the effect on surface microhardness as the atomic percentage of silver increases. It shows that at silver levels below 10 at. % the coating remains relatively hard compared to pure CrN. However, as the level of silver increases beyond 10 at. % the surface hardness drops to levels close to the bulk hardness of the substrate.

The invention claimed is:

1. A metallic biomedical article for use in contact with internal human or animal body tissue, having a first silver-containing metal nitride coating thereon,
   wherein the metal nitride coating is of $(A_x B_y C_z)$Q-Ag, where Q is selected from the group consisting of N, CN, BN, CBN, NO, CNO, BNO and CBNO, and
   wherein A, B and C are independently selected from the group consisting of Ti, Al, Cr, Ta, Y, W, Pt, Au, Cu, Si, Nb and B, and
   wherein $0.25 < x+y+z < 4.0$.

2. A metallic biomedical article according to claim 1, wherein the silver-containing metal nitride coating has been deposited by a PVD and/or CVD method.

3. A metallic biomedical article according to claim 1, wherein the first coating is a gradient coating with the silver content incremented or decreased towards the surface.

4. A metallic biomedical article according to claim 1, which comprises titanium, titanium alloys, zirconium, zirconium alloys, cobalt/chromium based alloys, stainless steel or mixtures thereof.

5. A metallic biomedical article according to claim 4, which is an implant, instrument or tool.

6. A metallic biomedical article according to claim 5, which is an orthopaedic implant.

7. A metallic biomedical article according to claim 6, where the implant is an articulating orthopaedic implant.

8. A metallic biomedical article according to claim 1, wherein the silver-containing metal nitride coating comprises from 0.1 to 99 wt % silver.

9. A metallic biomedical article according to claim 8, wherein the silver-containing metal nitride coating comprises from 0.5 to 35 wt % silver.

10. A metallic biomedical article according to claim 9, wherein the silver-containing metal nitride coating comprises from 1 to 25 wt % silver.

11. A metallic biomedical article according to claim 10 which has a second coating thereon.

12. A metallic biomedical article according to claim 10, wherein the second coating is a second silver-containing metal nitride coating on the outer surface of the component, and contains a greater amount of silver than the first silver-containing metal nitride coating.

* * * * *